(12) United States Patent
Schisler et al.

(10) Patent No.: US 8,623,390 B2
(45) Date of Patent: Jan. 7, 2014

(54) USE OF NOVEL STRAINS FOR BIOLOGICAL CONTROL OF PINK ROT INFECTIONS IN POTATO TUBERS

(75) Inventors: David A. Schisler, Morton, IL (US); Patricia J. Slininger, Metamora, IL (US); Tugba Adiyaman, Karsiyaka (TR)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 466 days.

(21) Appl. No.: 12/889,702

(22) Filed: Sep. 24, 2010

(65) Prior Publication Data

US 2012/0076765 A1    Mar. 29, 2012

(51) Int. Cl.
*A01N 25/00*  (2006.01)
*A01N 63/00*  (2006.01)
*A01N 65/00*  (2009.01)
*C12N 1/20*  (2006.01)

(52) U.S. Cl.
USPC ...... 424/405; 424/93.1; 424/93.4; 424/93.46; 424/93.47; 435/252.5; 435/253.3; 435/822; 435/832; 435/874

(58) Field of Classification Search
None
See application file for complete search history.

(56) References Cited

U.S. PATENT DOCUMENTS

| | | | | |
|---|---|---|---|---|
| 5,552,315 | A | * | 9/1996 | Slininger et al. ............ 435/253.3 |
| 6,107,247 | A | * | 8/2000 | Slininger et al. ............... 504/117 |
| 2006/0137042 | A1 | * | 6/2006 | Plesch et al. .................. 800/288 |

* cited by examiner

*Primary Examiner* — Debbie K Ware
(74) *Attorney, Agent, or Firm* — John Fado; Randall E. Deck; Lesley Shaw

(57) ABSTRACT

Six bacterial strains: *Bacillus simplex* strain 03WN13, *Bacillus simplex* strain 03WN23, *Bacillus simplex* strain 03WN25, *Pseudomonas koreensis* strain 10IL21, *Pantoea agglomerans* strain 10IL31, and *Pseudomonas lini* strain 13IL01, are superior antagonists of *Phytophthora erythroseptica* Pethybr., the causative agent of pink rot on potatoes. These bacterial strains are effective for suppression and control of pink rot on potatoes.

16 Claims, 1 Drawing Sheet

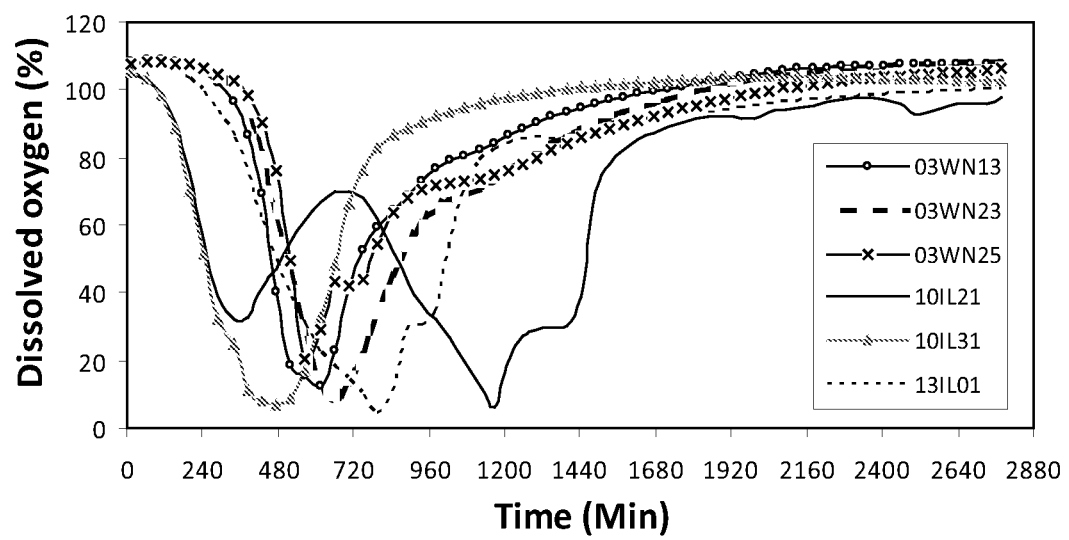

USE OF NOVEL STRAINS FOR BIOLOGICAL CONTROL OF PINK ROT INFECTIONS IN POTATO TUBERS

BACKGROUND OF THE INVENTION

1. Field of the Invention

The present invention relates to novel biological control agents for control of pink rot of potatoes.

2. Description of the Prior Art

Postharvest diseases of potatoes caused by fungal pathogens are a worldwide concern and can result in significant losses in the quality and quantity of potato tubers during storage, transport and the marketing process (Kotan et al. 2009. Biological control of the potato dry rot caused by *Fusarium* species using PGPR strains. Biol. Control 50:194-198). The causal agent of pink rot on potatoes, *Phytophthora erythroseptica* Pethybr., can cause particularly devastating disease effects on potatoes in storage. It was first reported as a soil borne storage disease in the United States in Maine in 1938 (Salas et al. 2000. The effect of wounding, temperature, and inoculum on the development of pink rot of potatoes caused by *Phytophthora erythroseptica*. Plant Dis. 84:1327-1333; and Wharton and Kirk. 2007. Pink Rot. Extension Bulletin, E-2993, Michigan Potato Diseases), and since then it has become widely distributed throughout North America as well as most potato-growing regions around the world (Taylor et al. 2006. Biological significance of mefenoxam resistance in *Phytophthora erythroseptica* and its implications for the management of pink rot of potato. Plant Dis. 90:927-934).

*P. erythroseptica* invades the potato plant through the roots and mainly infects tubers at the stem end through stolons previously infected by germinating oospores or zoospores. Although tubers infected with the pathogen usually are found in wet, low lying areas of fields during harvest [Al-Mughrabi et al. 2007. In-furrow applications of metalaxyl and phosphite for control of pink rot (*Phytophthora erythroseptica*) of potato in New Brunswick, Canada. Plant Dis. 91:1305-1309)] the disease can also develop in sandy soils without excessive moisture (Wharton and Kirk. 2007, ibid). Tubers can also be infected by *P. erythroseptica* through lenticels and buds as well as wounds that occur during harvesting. High relative humidity combined with poor air circulation and cool temperatures in storage promote pathogen survival and facilitate the infection of additional tubers (Atallah and Stevenson. 2006. A methodology to detect and quantify five pathogens causing potato tuber decay using real-time quantitative polymerase chain reaction. Phytopathology 96:1037-1045; Benson et al. 2009. *Phytophthora erythroseptica* (pink rot) development in Russet Norkotah potato grown in buffered hydroponic solutions I. calcium nutrition effects. Am. J. Potato Res. 86:466-471; and Salas et al. 2000, ibid). Pink rot infection is usually associated with secondary infection by anaerobic soft rot bacteria and further losses may occur in storage due to bacterial infection of damaged tissue (Wharton and Kirk. 2007, ibid).

Most potato cultivars commonly grown in North America are susceptible to pink rot (Salas et al. 2003. Assessment of resistance of tubers of potato cultivars to *Phytophthora erythroseptica* and *Pythium ultimum*. Plant Dis. 87:91-97). A survey of North American cultivars with fungal disease resistance showed that over 25% of 130 cultivars released have resistance to one or more fungal diseases such as early dying, late blight, early blight, dry rot and black scurf, but notably, resistance to pink rot and silver scurf was absent (Secor and Gudmestad. 1999. Managing fungal diseases of potato. Can. J. Plant Pathol. 21:213-221).

Measures for managing pink rot in the field and in storage includes planting in soils with good water drainage, crop rotation, harvesting tubers at temperatures below 18° C., using high airflows and preventing water condensation in the tuber pile during storage, eliminating diseased tubers, and the timely application of mefenoxam-based fungicides (Miller et al. 2006. Post harvest applications of zoxamide and phosphite for control of potato tuber rots caused by oomycetes at harvest. Am. J. Potato Res. 83:269-278; Salas et al. 2000. ibid; and Secor and Gudmestad. 1999. ibid). Many studies suggest that mefenoxam-resistant isolates of *P. erythroseptica* are now widespread, which likely explains the failure of these chemicals to consistently control pink rot (Benson et al. 2009. ibid; and Taylor et al. 2006. ibid) and points to the need to develop additional methods for reducing new pink rot infections in storage.

Infections by *P. erythroseptica* initiated after tuber harvest are difficult to control. Studies using phosphorous acids and various salts in furrow have shown the potential of these materials to reduce pink rot on harvested tubers (Johnson. 2008. Post-harvest applications of phosphorous acid materials for control of *Phytophthora infestans* and *Phytophthora erythroseptica* on potatoes. Plant Pathol. 7:50-53; Miller et al. 2006. ibid; and Mills et al. 2005. Salt compounds as control agents of late blight and pink rot of potatoes in storage. Can. J. Plant Pathol. 27:204-209), but additional disease reduction technologies for this purpose are still needed. With growing public interest in reducing chemical pesticide residues in food and the environment, the need to develop new pest management technologies that reduce the use of chemical pesticides is apparent.

Several studies have been conducted on the biological control of economically important soil borne storage diseases of potatoes, including studies where microbial strains from various suppressive soils were found to be active against *Fusarium* dry rot (Schisler and Slininger. 1994. Selection and performance of bacterial strains for biologically controlling *Fusarium* dry rot of potatoes incited by *Gibberella pulicaris*. Plant Dis. 78:251-255; and Schisler et al. 2000. Potato cultivar, pathogen isolate and antagonist cultivation medium influence the efficacy and ranking of bacterial antagonists of *Fusarium* dry rot. Biocontrol Sci. and Technol. 10: 267-279) and late blight (Hollywood. 2008. Biological Control of Late Blight of Potatoes: in vivo and in vitro evaluation of microbial antagonists against tuber blight, Ph.D. Dissertation, University of London, Biology Department, London, England; and Slininger et al. 2007. Biological control of post-harvest late blight of potatoes. Biocontrol Sci. and Technol. 17:647-663) on tubers in storage. However, research on discovering biological control agents that are specifically targeted against pink rot on stored potato tubers is limited (Schisler et al. 2009. Bacterial antagonists, zoospore inoculum retention time and potato cultivar influence pink rot disease development. Am. J. Potato Res. 86:102-111).

However, despite these and other advances, there is a continuing need for improved biocontrol agents for pink rot.

SUMMARY OF THE INVENTION

We have now discovered six bacterial strains which are superior antagonists of *Phytophthora erythroseptica* Pethybr., the causative agent of pink rot on potatoes. These six bacterial strains include *Bacillus simplex* strain 03WN13, *Bacillus simplex* strain 03WN23, *Bacillus simplex* strain 03WN25, *Pseudomonas koreensis* strain 10IL21, *Pantoea agglomerans* strain 10IL31, and *Pseudomonas lini* strain 13IL01. These bacterial strains are effective for suppression and control of pink rot on potatoes, including potatoes in the field and under storage conditions.

In accordance with this discovery, it is an object of this invention to provide novel bacterial strains which are superior antagonists of *Phytophthora erythroseptica* Pethybr., the fungus responsible for pink rot on potatoes.

Another object of this invention is to provide novel bacterial strains which are effective for suppressing pink rot on potatoes.

Yet another object of this invention is to provide novel bacterial strains which are effective for suppressing pink rot on potatoes in the field or during postharvest storage.

A further object of this invention is to provide novel bacterial strains which demonstrate favorable liquid culture growth kinetics in commercially feasible culture media.

These and other objects of the invention will become readily apparent from the ensuing description.

BRIEF DESCRIPTION OF THE FIGURES

FIG. 1 shows the oxygen consumption by the six bacterial antagonists of pink rot grown in shake flask liquid culture for 48 h. Oxygen sensors in flasks enabled real time monitoring of the percentage of dissolved oxygen present in liquid broths. The data presented was used to calculate the time when isolate culture broths commenced recovery from oxygen depletion (DT).

DETAILED DESCRIPTION OF THE INVENTION

The expression "superior antagonist" used herein in reference to a microorganism is intended to mean that the subject strain exhibits a degree of inhibition of fungal-induced potato disease (i.e. proliferation of an agent responsible for the disease) exceeding, at a statistically significant level, that of an untreated control.

The six bacterial strains of this invention, *Bacillus simplex* strain 03WN13, *Bacillus simplex* strain 03WN23, *Bacillus simplex* strain 03WN25, *Pseudomonas koreensis* strain 10IL21, *Pantoea agglomerans* strain 10IL31, and *Pseudomonas lini* strain 13IL01, were isolated in pure form from soil samples. The isolated strains were identified using 16S gene sequence homologies with known strains as described in Example 1. The isolated strains exhibit morphological, cultural, and biochemical properties consistent with the respective type strains of these *Bacillus*, *Pantoeae*, and *Pseudomonas* species as described in Bergey's Manual of Determinative Bacteriology (Holt et al., 1994), and by Kwon et al. (2003. *Pseudomonas koreensis* sp. nov., *Pseudomonas umsongensis* sp. nov. and *Pseudomonas jinjuensis* sp. nov., novel species from farm soils in Korea. Int. J. Syst. Evol. Microbiol. 53:21-27), and Delorme et al. (2002. *Pseudomonas lini* sp. nov., a novel species from bulk and rhizospheric soils. Int. J. Syst. Evol. Microbiol. 52:513-523), the contents of each of which are incorporated by reference herein. All six isolates of this invention, *Bacillus simplex* strains 03WN13, 03WN23, and 03WN25, *Pseudomonas koreensis* strain 10IL21, *Pantoea agglomerans* strain 10IL31, and *Pseudomonas lini* strain 13IL01, have been deposited in the general collection of the Agricultural Research Service Culture Collection (NRRL), 1815 N. University St., Peoria, IL, 61604, USA. All six isolates of this invention, *Bacillus simplex* strain 03WN13 (NRRL general collection accession no. B-59398), *Bacillus simplex* strain 03WN23 (NRRL general collection accession no. B-59399), *Bacillus simplex* strain 03WN25 (NRRL general collection accession no. B-59400), *Pseudomonas koreensis* strain 10IL21 (NRRL general collection accession no. B-59401), *Pantoea agglomerans* strain 10IL31 (NRRL general collection accession no. B-59402), and *Pseudomonas lini* strain 13IL01 (NRRL general collection accession no. B-59404), have also been deposited on Sep. 12, 2011 under the provisions of the Budapest Treaty in the Agricultural Research Service Culture Collection (NRRL), 1815 N. University St., Peoria, IL, 61604, USA, and have been assigned Deposit Accession Nos. NRRL B-50565, NRRL B-50566, NRRL B-50567, NRRL B-50568, NRRL B-50569 and NRRL B-50570, respectively.

Propagation of the bacterial antagonists for use may be effected by culture under any conventional conditions and in media which promote their growth. A variety of known culture media are suitable for use herein for the production of the bacterial antagonists of the invention. As a practical matter, and without being limited thereto, the bacteria antagonists are typically grown in aerobic liquid cultures on media which contain sources of carbon, nitrogen, and inorganic salts assimilable by the microorganism and supportive of efficient cell growth. Preferred carbon sources are hexoses such as glucose, but other assimilable sources include glycerol, amino acids, xylose, etc. Many inorganic and proteinaceous materials may be used as nitrogen sources in the growth process. Preferred nitrogen sources are amino acids and urea, but others include gaseous ammonia, inorganic salts of nitrate and ammonium, vitamins, purines, pyrimidines, yeast extract, beef extract, proteose peptone, soybean meal, hydrolysates of casein, distiller's solubles, and the like. Among the inorganic minerals that can be incorporated into the nutrient medium are the customary salts capable of yielding calcium, zinc, iron, manganese, magnesium, copper, cobalt, potassium, sodium, molybdate, phosphate, sulfate, chloride, borate, and like ions. Similarly, suitable pH and temperature conditions are also variable, and optimal conditions will of course vary with the particular strain. However, cell growth of the bacteria can typically be achieved at temperatures between 1° and 37° C., with the preferred temperature being in the range of 15° and 30° C. The pH of the nutrient medium can vary between 4 and 9, but the preferred operating range is 6-8. The bacteria should be cultivated under aerobic conditions, preferably with agitation. The total time for the culture will be dependent on the strain, and cultivation conditions, particularly the culture medium, temperature, and aeration. For the purpose of illustration and without being limited thereto, the culture of the strain is typically harvested 72 hr after inoculation when grown at 25° C., but may be as early as 20 to 24 hr, especially when grown under conditions leading to more rapid growth, such as higher temperatures (26-30° C.) or on certain media with ingredients that are more rapidly metabolized.

Following cultivation, the resultant culture of the bacterial antagonists is recovered for subsequent use. Although it is envisioned that crude preparations of the bacteria in culture media may be used directly, in a preferred embodiment the bacteria are harvested and formulated as described herein below.

The bacterial antagonists of this invention are effective for controlling, that is reducing the incidence or severity of pink rot (caused by *Phytophthora erythroseptica* Pethybr.) on potatoes, in comparison to untreated controls. The bacterial antagonists of the invention can be applied by any conventional method to the surfaces of potato tuber materials, to include without limitation, whole potato tubers, potato tuber parts, or seed tubers. For example, they can be applied as an aqueous spray or dip, as a wettable powder, or as a dust. Formulations designed for these modes of application will usually include a suitable liquid or solid carrier together with other adjuvants, such as wetting agents, sticking agents and the like. Starch, polysaccharides, sodium alginate, cellulose, etc. are often used in such formulations as carriers and sticking agents, and are suitable for use herein as well.

As the desired effect is control of the fungal disease pink rot of potatoes, the expressions "an effective amount" and "a suppressive amount" are used herein in reference to that quantity of antagonist composition which is necessary to obtain a statistically significant reduction in the level of pink rot (measured as a decrease in the severity or the rate of incidence) relative to that occurring in an untreated control under suitable conditions of treatment as described herein. Without being limited thereto, the actual rate of application of a liquid formulation will typically vary from a minimum of about $1 \times 10^3$ to about $1 \times 10^{10}$ total viable cells/ml and preferably from about $1 \times 10^6$ to about $1 \times 10^9$ total viable cells/ml, assuming a mode of application which would achieve substantially uniform contact of at least about 90% of the potato surface. If the composition is applied as a solid formulation, the rate of application should be controlled to result in a comparable number of viable cells per unit area of potato surface as obtained by the aforementioned rates of liquid treatment.

It is envisioned that the temperatures at which the bacterial antagonists are effective would range from about 5° C. to about 30° C. The preferred temperature range is 10° to 25° C., and the optimal range is considered to be 12° to 20° C. Therefore, the bacteria can theoretically be applied at any time during the harvest, grading, or shipping process, or during the early stages of storage. Of course, potato tubers are more susceptible to infection any time a wound occurs and the fungal disease agent is present. Therefore, the longer the delay between the tuber wounding and the treatment with the bacterial composition, the greater the chance the pathogen will successfully infect the tuber. Though we have previously demonstrated that delays of 4 h between wounding and treatment do not significantly affect antagonist performance, it is anticipated that longer delays may decrease the effectiveness of the treatment depending on methods of cell formulation and application. For field applications, the bacterial antagonists may be applied directly onto the seed tubers or pieces thereof as described above prior to or during planting. It is also envisioned that the bacterial antagonists may be applied to the soil in the locus of the seed tubers being planted, such as in the furrows.

The following example is intended only to further illustrate the invention and is not intended to limit the scope of the invention which is defined by the claims.

EXAMPLE 1

The microbiota of 84 different agricultural soils was transferred to separate samples of a gamma irradiation-sterilized field soil enriched with potato periderm and the resulting soils were assayed for biological suppressiveness to *Phytophthora erythroseptica* and their effect on zoospore production. The 13 most suppressive soil samples, which reduced zoospore production by 14 to 93% and disease severity on tubers by 6 to 21%, were used to isolate 279 organisms. Fourteen strains that reduced pink rot infections in preliminary tests were selected for further study. Six bacterial strains that reduced the severity of disease (P≤0.05, FPLSD) in subsequent tests were retained and identified. Relative performance indices (RPIs) for biocontrol efficacy and for each of four kinetic parameters including total colony forming units ($CFU_{max}$), biomass production values ($DW_{max}$), cell production after 8 hours (ODO) and time of recovery from oxygen depletion (DT) were calculated for each strain. Overall $RPI_{EffKin}$ values for each strain then were calculated using strain RPI values for both efficacy ($RPI_{Eff}$) and kinetics ($RPI_{Kin}$). Strains with the highest $RPI_{EffKin}$ possess the best biocontrol efficacy of the strains tested and liquid culture growth characteristics that suggest commercial development potential.

Materials and Methods

Tuber Source and Handling

Russet Norkotah and Russet Burbank tubers obtained from the University of Wisconsin's Seed Potato Certification Program (Rhinelander, Wis.) were used to assay soil suppressiveness and the efficacy of bacterial isolates against *P. erythroseptica* respectively. Tubers were stored at 5° C. and approximately 95% RH. Tubers were washed gently with distilled water, allowed to air-dry and warmed to room temperature on laboratory benches for 16 h prior to use in bioassays.

Production of Pathogen Inoculum

*Phytophthora erythroseptica* strain PE 02-25 was obtained from the laboratory of J. S. Miller (Miller Research LLC, Rupert, Id.). Sporangia capable of liberating zoospores were produced according to the method of Miller et al. (ibid) as modified by Schisler et al. (2009. ibid).

Assay to Detect Microbial Communities Suppressive to Pink Rot

Soil samples were obtained from 84 different agricultural soils, primarily recently grown to potatoes, in the States of Wisconsin, Washington and Illinois. Microbial communities from these soils then were assayed for ability to suppress sporangia production, and post-harvest pink rot disease development incited by *P. erythroseptica*. To accomplish this, approximately 100 g of field soil samples were sieved through 2-mm screens and stored at 4° C. in loosely closed plastic bags until needed. Individual field soil samples then were combined with powdered, heat sterilized potato periderm and γ irradiation sterilized (5 megarads minimum) sandy loam field soil (5:2:93 w/w/w respectively) in plastic bags. Moist soil mixtures in plastic bags were adjusted to approximately 9-10% moisture ([w-d]/d) and shaken periodically during incubation for 1 week at 15° C. Moisture content of preparations was confirmed using a moisture analyzer (OMNIMARK Instrument Corp., Temple, Ariz.). After incubation, soil mixtures were prepared for bioassay according to the method of Schisler and Slininger (1994. ibid) with some modifications. Extracts of soil mixtures were produced by adding 100 ml of distilled water to 20 g of mixture (containing approximately 1 g of the sieved field soil) in 500 ml flasks and incubating the flasks in a rotary shaker incubator (Inova 4230, New Brunswick Scientific, Edison, N.J.) at 15° C. and 250 rpm for approximately 18 h. After the incubation period, soil suspensions were allowed to settle on ice for 1 hour, and then the aqueous soil extract was removed.

To determine the ability of the microbial communities in soil extracts to suppress zoospore production by *P. erythroseptica*, 10 ml of each soil extract was dispensed into Petri plates containing a hyphal mat of *P. erythroseptica* (Millet et al. 2006. ibid; Schisler et al. 2009. ibid) and the plates incubated in darkness at 18° C. for 2 days. The counts of sporangia and zoospores of all flooded plates were then evaluated. Two replicates were used for each extract and approximately 16 extracts were tested per experiment, resulting in a total of six experiments.

The same extracts were also individually tested for ability to reduce pink rot disease by combining extracts and zoospores of *P. erythroseptica*. Prior to use in bioassays each of the aqueous soil extracts were mixed with an equal volume of pathogen inoculum suspension that was adjusted with sterile soil extract to a concentration of $5 \times 10^4$ zoospores/ml. This inoculum concentration incites severe disease pressure and resulted in a high level of disease severity as determined by lesion size in the bioassay used in these studies. Russet Norkotah tubers were punctured with a blunted nail to produce a wound that was 1 mm wide by 2 mm deep to simulate tubers wounded during harvesting and loading into storages. All assays were conducted by introducing 5 µl of a soil extract and zoospore suspension into a wound. Controls were inoculated with a mixture of sterile soil extract which was prepared according to the method of Schisler et al., (2009. ibid) and pathogen inoculum. A strain that can reduce *Fusarium* dry rot, late blight, pink rot and sprouting in storage (*Enterobacter cloacae* S11:T:07, Secor. 1999. ibid) was used as an active antagonist control in all assays. Each tuber contained 2 wounds and was inoculated by a soil extract treatment or a control treatment. Six replicate tubers per potato assay treatment were arranged by repeating the entire inoculation scheme using the same randomized order of soil extracts.

Tubers were incubated in the dark at near 100% relative humidity in trays covered by aluminum foil and enclosed in a large plastic bag for 1 week at 15° C., the temperature at which biocontrol agents would be expected to perform in commercial tuber storage houses immediately after loading tubers into storages. The periderm was then removed from tubers and the sum of the length and width (in mm) of pink rot lesions surrounding the wounds was recorded. Extracts which were the most effective in reducing disease across all assays were chosen by calculating, for each experiment, the treatment effect compared to the corresponding control (%), and then pooling data sets. For both zoospore reduction and pink rot disease experiments, data sets were subjected to analysis of variance and the means separated using Fisher's protected LSD, (FPLSD, $P \leq 0.05$). Extracts that reduced sporangia production or pink rot to the greatest extent compared to their respective controls were selected for isolating individual microbial strains.

Isolation of Microorganisms

All of the soil extracts that were tested for suppressiveness to zoospore production and ability to reduce pink rot disease were stored immediately at −80° C. after combining the extract with sterile 50% glycerin at a ratio of 80:20, respectively. After the zoospore production and pink rot disease assays, data were analyzed to identify soil extracts that were the most effective in reducing zoospore production or pink rot disease compared to controls. The most suppressive soil extracts were then thawed and serial dilutions prepared in 0.004% phosphate buffer (pH 7.2) with 0.019% $MgCl_2$. Dilutions were spread on plates of one-tenth strength tryptic soy agar (TSA/10, Difco Laboratories, Detroit, Mich.) that contained cycloheximide (0.05 g/L); one-quarter strength potato-dextrose agar (PDA/4, Difco) that contained 0.05 g/L cycloheximide and acidified yeast malt extract agar (YME), (3.0 g/L yeast extract, 3.0 g/L malt extract, 5.0 g/L peptone (type III), and 0.1 g/L chloramphenicol, acidified with 1 M HCl to pH 3.7 after autoclaving). Additionally, separate dilutions of each extract were heat shocked for 12 minutes at 80° C. and plated on 1/5 TSA (TSA/5) to select for spore forming bacteria such as *Bacillus* spp. After incubation for 2 days at 28° C., colony counts of organisms were made and several isolates of each morphologically distinct colony type from each medium were isolated in pure culture. A total of 279 bacterial isolates were streaked for purity and stored at −80° C. in 10% glycerol.

Assay of Efficacy of Bacterial Isolates Against *P. Erythroseptica*

One hundred morphologically distinct isolates were produced in a semidefined complete liquid medium (SDCL) (Slininger et al. 1994. Two-dimensional liquid culture focusing: a method of selecting commercially promising microbial isolates with demonstrated biological control capability. Pages 29-32 in: Improving Plant Productivity with Rhizosphere Bacteria. M. H. Ryder, P. M. Stephens, and G. D. Bowen, eds. The 3rd International Workshop on Plant Growth-Promoting Rhizobacteria, 1994, Mar. 7-11, Adelaide, S. Australia. Glen Osmond, South Australia: CSIRO Division of Soils), and evaluated for efficacy in reducing pink rot disease. Samples of pure isolates frozen at −80° C. in 10% glycerol were streaked for purity onto one-fifth strength tryptic soy agar (TSA/5, pH 6.8). After 24 h incubation at 28° C., cells were removed from the surface of colonized plates using sterile cotton swabs and utilized to initiate liquid medium pre-cultures of each isolate. Ten ml of SDCL in 50 ml Erlenmeyer flasks were inoculated to obtain slightly turbid suspensions (optical density of approximately 0.170 at 620 nm wavelength light ($A_{620}$)) for pre-cultures of each isolate. Pre-cultures were then incubated in a rotary shaker incubator at 25° C. with a throw of 2.5 cm and 250 rpm for 24 h. Pre-cultures of each isolate were used to inoculate test cultures composed of ten ml of SDLC in 50 ml Erlenmeyer flasks to an optical density of 0.1 $A_{620}$. Test cultures were incubated as described for pre-cultures, harvested after 48 h, diluted to 1/10 strength and tested in separate experiments on Russet Burbank potato tubers to evaluate the efficacy of isolates in reducing pink rot disease according to the protocol described earlier. The diluted antagonist cell concentration utilized varied between $10^6$-$10^9$ cfu/ml depending on the cell concentration achieved by 48 h cultures. By comparing strains using a dose that is based on a standard dilution of colonized culture broth regardless of the number of cells this represents, the efficacy of strains is compared on an identical "cost of production" basis. Total pink rot lesion size was measured and the percent disease reduction relative to the control was determined for each experiment. There were 6 replicate wounds inoculated for each treatment. Approximately 20 different strains were tested in each experiment. The top 14 antagonists from these experiments were then tested again in additional replicated experiments to confirm isolate efficacy against pink rot. Because experiment by treatment interactions were insignificant, (P=0.91) data were pooled across experiments, analysis of variance conducted, and the statistical significance of the difference in the means was assessed using FPLSD ($P \leq 0.05$).

Bacterial Identifications

Six bacterial strains which reduced the severity of pink rot were identified according to the method of Rooney et al. (Rooney et al. 2005. Bacterial species diversity in cigarettes linked to an investigation of severe pneumonitis in U.S. military personnel deployed in operation Iraqi freedom. Curr. Microbiol. 51:46-52; and Rooney et al. 2009. Phylogeny and molecular taxonomy of the *Bacillus subtilis* species complex and description of *Bacillus subtilis* subsp. *inaquosorum* subsp. *nov*. Int. J. Syst. Evol. Microbiol. 59:2429-2436). This method is summarized as follows. To taxonomically identify each individual soil isolate, the 16S gene was sequenced (see below) and the phylogenetic position was determined relative to the type strains of closely related sequences identified by using the SeqMatch program in the Ribosomal Database Project (Wang et al. 2007. Reclassification of *Bacillus axarquiensis* Ruiz-Garcia et al. 2005 and *Bacillus malacitensis* Ruiz-Garcia et al. 2005 as later heterotypic synonyms of

*Bacillus mojavensis* Roberts et al. 1994. Int. J. Syst. Evol. Microbiol. 57:1663-1667). The nucleotide sequences of these type strains were subsequently downloaded from GenBank and aligned to the 16S sequence of the isolate in question using the program ClustalX (Thompson et al. 1997. The CLUSTAL-X windows interface: flexible strategies for multiple sequence alignment aided by quality analysis tools. Nucleic Acids Res. 25:4876-4882). A phylogenetic analysis was then conducted using the neighbor-joining method as implemented in the computer program MEGA4 (Tamura et al. 2007. MEGA4: Molecular Evolutionary Genetics Analysis (MEGA) software version 4.0. Molecular Biol. and Evol. 24:1596-1599) to determine the phylogenetic placement of each isolate relative to the type strains. Kimura two-parameter distances (Kimura. 1980. A simple method for estimating evolutionary rates of base substitutions through comparative studies of nucleotide sequences. J. Mol. Evol. 16:111-120) were computed for all possible strain/species comparisons and used to generate phylogenetic trees with the neighbor-joining method as implemented in the computer program MEGA4 (Tamura et al. 2007. ibid). The statistical reliability of internal branches was assessed from 1,500 bootstrap pseudoreplicates. If the isolate and a particular type strain clustered with a bootstrap value of 90% or greater and displayed a similarity of 97% or more with respect to their 16S rRNA gene sequence divergence, then the isolate was considered to be a member of that particular species. The fragment of the 16S rRNA gene that was analyzed corresponded to positions 27 to 1387 of the *E. coli* 16S rRNA. Polymerase chain reaction (PCR) amplifications were performed with 1 unit of Amplitaq DNA Polymerase (Invitrogen Life Technologies, Carlsbad, Calif.), 2.5 mM $MgCl_2$, 200 μM dNTPs, 1.0 μM each of forward and reverse oligonucleotide primers, 1× reaction buffer, and 50 to 100 ng template DNA. The universal oligonucleotide primers 27f (Lane. 1991. 16S/23S rRNA sequencing. Pages 115-175 in: Nucleic Acid Techniques in Bacterial Systematics. E. Stackebrandt and M. Goodfellow, eds. Chichester: Wiley) and 1387r (Marchesi et al. 1998. Design and evaluation of useful bacterium-specific PCR primers that amplify genes coding for bacterial 16S rRNA. Appl. Environ. Microbiol. 64:795-799) were used to amplify and sequence the 16S rRNA gene. All PCR reactions were performed for 35 cycles, each consisting of a 30 sec. denaturation step at 94° C., a 30 sec. annealing step at 54° C., and a 1 min. extension step at 72° C. Amplification products were purified using Montage PCR Cleanup Filter Plates (Millipore, Billerica, Mass.). The forward and reverse strands of each fragment were sequenced using the Big Dye Kit (Applied Biosystems, Inc., Foster City, Calif.) on an ABI 3730 automated sequencer. The resulting DNA sequences were checked for errors through visual inspection of the chromatograms.

Determination of Antagonist Growth Kinetics in Liquid Culture Total Biomass Production and Colony Forming Units The productivity of the six most efficacious antagonists was evaluated based on biomass accumulation and colony forming unit (CFU) determinations. Antagonists were cultured on SDCL (Slininger et al. 1994. ibid). Briefly, a basal salts medium was supplemented with vitamins, nucleic acids, tryptophane, and cysteine and contained 15 g glucose $L^{-1}$ and 15 g acid hydrolyzed casein (vitamin-free Casamino acids) $L^{-1}$. The SDCL medium contained 14 g carbon $L^{-1}$ and had a carbon-to-nitrogen ratio of 11:1. To obtain cultures for these analyses, 6 mL precultures of the various isolates were incubated in SDCL medium in 50 mL Erlenmeyer flasks at 25° C. and 250 rpm in a rotary shaker incubator. Fermentation broth from 24 h precultures was used to inoculate a 50 mL test culture in a 250 mL Erlenmeyer flask, as described previously. Test cultures were grown for four days at 25° C. and 250 rpm in a rotary shaker incubator. For biomass accumulation studies, cells were separated from the 50 mL culture broth using a prewashed, dried and weighed 47 mm diameter, cellulose nitrate membrane (0.45 μm pore size, manufacturer) on a Fisherbrand vacuum filtration apparatus (Fisher Scientific Inc, Pittsburgh, Pa.). After the supernatant was removed, biomass retained on the filter was washed two times with 2 ml of deionized water. The membranes were then dried at 105° C. in an oven for 1.5-2.0 h to a constant weight (±0.0005 g), allowed to cool to room temperature in a desiccator, reweighed, and the dry weight values ($DW_{max}$) were calculated. Total CFU/ml ($CFU_{max}$) were determined by plating serial dilutions of 48 h culture broths on TSA/5. Three replicates were used for all treatments and all experiments were repeated at least once.

Oxygen Utilization During Growth of Antagonists in Liquid Culture

By monitoring real time DO in liquid cultures, the onset of unbalanced growth can be estimated by determining when DO levels begin to recover to fully saturated levels. Strains that rapidly complete the process of converting nutrients to biomass would require less fermentation time and therefore would be less expensive to produce. To estimate the time when cultures had achieved near maximal cell counts, the time of recovery from maximum oxygen depletion (DT) was determined for the six pink rot antagonists. Thirty ml cultures of each of the six pink rot antagonists were grown for 48 hours in 250 mL shake flasks at 25° C. and 250 rpm in a rotary shaker incubator. A miniaturized oxygen sensor was attached on the bottom of each flask and the shake flask holders equipped with monitors which permitted real-time oxygen concentration measurement without stopping agitation or removing flasks from the incubator (SFR v2 shake flask reader, PSt3 sensor, PreSens Precision Sensing GmbH, Regensburg, Germany). Oxygen concentrations were measured every 15 minutes and data transmitted via Bluetooth to a computer with SFR v2 software (Prescens Precision Sensing). Oxygen concentration data were computed as "% oxygen" based on 100% oxygen at the start of fermentation (time 0). Mean oxygen concentration values for each isolate were used to generate three separate oxygen utilization curves from three separate experiments, and DT values determined for each isolate in each experiment.

Cell Production after 8 Hours

To estimate the ability of strains to rapidly produce cells in liquid culture, the optical density of test cultures was determined 8 hours after inoculation. Liquid cultures were produced in standard shake flask cultures as described earlier. There were three replicate flasks per experiment, experiments were conducted three times and data from repeated experiments were pooled for data analysis.

Relative Performance Indices (RPI)

A relative performance index (RPI) for each bacterial isolate was calculated for each of the four kinetic parameters used to quantify isolate growth in liquid culture as well as for the relative performance efficacy ($RPI_{Eff}$) of the isolates. Given that data values are normally distributed for the parameter tested, the value of $F=(X-X_{avg})/s$ ranges from −2 to +2. Here, X designates a single datum value observed for a bacterial strain, and $X_{avg}$ and s are the average and standard deviation respectively, of all values observed for all bacteria for the individual parameter being tested. Using the formula $RPI=[(F+2)*100/4]$, data corresponding to each parameter type were converted to dimensionless indices with a theoretical range of 0-100. Note that the inverted term (2-F) was used in the calculation of $RPI_{Eff}$ and $RPI_{DT}$ instead of (2+F), because lower disease ratings and DT values represent favorable characteristics that should therefore be associated with higher RPI values. The overall $RPI_{Kin}$ values for each bacterial isolate were obtained by subjecting the RPI values obtained for each kinetic parameter to ANOVA and mean separation using Fisher's protected LSD test (P≤0.05). RPI values for both biocontrol efficacy and kinetics for each strain were similarly analyzed to determine a commercial potential ranking of the six antagonists evaluated. Strains with the highest overall RPI when considering both efficacy and kinetics ($RPI_{Eff, Kin}$) possess the best biocontrol efficacy of the strains tested and liquid culture growth characteristics that suggest strong commercial development potential.

Results

Isolation of Microorganisms

Of the 84 samples tested, extracts of 13 soils showed indications of reducing pink rot disease severity on Russet Norkotah tubers and/or reducing *P. erythroseptica* zoospore production compared to controls and were selected as substrates for the isolation of individual microbial strains (Table 1). The soil extracts selected reduced zoospore production by as much as 93% and pink rot disease severity on tubers by as much as 21%.

A total of 279 isolates of bacteria and yeast were recovered from the serial dilutions of the soil extracts (Table 1). One hundred twenty-one isolates were recovered on PDA/4 medium, 92 isolates from TSA/10, 57 heat tolerant isolates from TSA/5 and 9 isolates from acidified YME agar. Of these strains, 100 were selected for initial evaluation of strain efficacy in reducing new pink rot infection on stored potato tubers. Strains possessing visibly different colony morphologies were selected from dilutions of each of the 13 soil extracts. Fourteen of the 100 microbial strains reduced pink rot in preliminary tests (data not shown) and were selected for additional study.

Isolate Efficacy Against *P. Erythroseptica* and Relative Performance Indices

The 14 putative antagonists that reduced pink rot disease in preliminary assays were tested in two replicated experiments. Because experiment by treatment interactions were not statistically significant (P=0.91), data were pooled across experiments and analysis of variance conducted. In comparison to the control tubers inoculated with *P. erythroseptica*, six of the 14 bacterial strains reduced disease (P≤0.05, FPLSD) (Table 2). *Enterobacter cloacae* S11:T07 (NRRL B-21050) which can reduce pink rot in storage, was not effective in reducing new pink rot infections under the experimental conditions of the present study. *Bacillus simplex* strains 03WN13, 03WN23 and 03WN25 reduced pink rot lesion size by 30, 27 and 32%, respectively, while *Pantoea agglomerans* 10IL31 and *Pseudomonas* lini 13IL01 reduced lesion size by 33 and 26%, respectively. Though *Bacillus cereus* strain 03WN09 reduced pink rot disease development by 28%, the strain was eliminated from further consideration since some strains of this species have been associated with causing illness in humans (Drobniewski. 1993. *Bacillus cereus* and related species. Clin. Microbiol. Rev. 6: 324-338). Strain 10IL21, which was the next best strain in reducing disease after the six strains that were initially selected (24% reduction in severity versus the control), was therefore included with the other five antagonistic strains for further evaluation and kinetic analyses. A relative performance index (RPI) was calculated based on the efficacy of each of six bacterial antagonists assayed against *P. erythroseptica* on the cultivar Russet Burbank (Table 3). The most effective isolates in reducing pink rot were 10IL31 and 03WN25 which allowed 39 mm and 39.4 mm diseased tissue respectively compared with an average of 58.4 mm for control tubers inoculated with the pathogen alone (Table 3). The six antagonists were similarly effective in reducing pink rot as shown by similar $RPI_{Eff}$ values. The six antagonists originated from one of three soil extracts, all of which were effective in reducing zoospore production by 85% or more (Tables 1, 2).

Bacterial Identifications

Selected microbial strains that significantly inhibited disease development incited by *P. erythroseptica* were identified as *Bacillus simplex* (3 isolates), *Pseudomonas koreensis*, *Pseudomonas lini* and *Pantoea agglomerans* (Table 2) and the six strains were deposited in the ARS Culture Collection (NRRL) [http://nrrl.ncaur.usda.gov].

Antagonist Growth Kinetics in Liquid Culture and Relative Performance Indices

The liquid culture kinetic performance of the six antagonists varied considerably as seen in the means (Table 4) and RPI analysis of each of the four kinetic parameters tested (Table 5, P≤0.05, FPLSD). *Bacillus simplex* strains 03WN13 and 03WN23 had the highest biomass production value (DW-max) of the six strains and were significantly more productive than the other four strains tested based on RPI analysis (Table 5, P≤0.05, FPLSD). Strains 10IL21, 10IL31 and 13IL01 (*Pseudomonas koreensis*, *Pantoea agglomerans* and *Pseudomonas lini* respectively) produced more CFU/ml in liquid culture than the other three strains (Table 4), with strain 10IL21 producing more CFU/ml than any other strain (Table 4, P≤0.05, FPLSD). The ranks of the antagonists for these two parameters were not always closely aligned. For example, strain 10IL21 ranked first in CFU/ml production but sixth in biomass production ($DW_{max}$) (Tables 4, 5). Data on the time of culture medium recovery from oxygen depletion (DT) (and onset of unbalanced growth) showed that the three *Bacillus* strains 03WN13, 03WN23 and 03WN25 and *P. agglomerans* strain 10IL31 had the lowest DT values (Table 4, FIG. 1) indicating that these strains rapidly exhausted one or more nutrients critical to growth in liquid culture. The DT RPI value for strain 10IL31 was higher than any other except strain 03WN13 (Table 5, P≤0.05, FPLSD). As shown in Table 4, the results of cell production after 8 h (OD0 for the six strains generally exhibited the same trends as the DW max data. *Bacillus simplex* strains 03WN13 and 03WN23 obtained the two highest $OD_8$ values (Table 5) and their associated RPI values were higher than all but one of the other four strains tested (Table 5, P≤0.05, FPLSD). Because no strain exhibited consistently high performance across all of the kinetic parameters measured, overall $RPI_{Kin}$ values did not differ significantly (P≤0.05, FPLSD, Table 5). Strain 03WM13 had the highest ranking overall $RPI_{Kin}$ value of 64.1 while strain 10IL21 had the lowest ranking overall $RPI_{Kin}$ value of 35.9 (Table 5).

Ranking of Strain Potential for Development as a Pink Rot Biological Control Agent Overall $RPI_{Eff, Kin}$ values were calculated by averaging $RPI_{Eff}$ and $RPI_{Kin}$ values. Values ranged from 57.6 to 48.8 for strains 03WM13 and 13IL01, respectively (Table 6) but did not differ statistically (P≤0.05, FPLSD). Based on the ranking of the strains $RPI_{Eff, Kin}$ values, strains *Bacillus simplex* 03WM13 and *Pantoea agglomerans* 10IL31 possess the best combination of efficacy and desirable liquid culture growth kinetics of the six strains studied.

Discussion

In the present effort to isolate putative antagonists of pink rot, we recovered 279 isolates of bacteria and yeast from 13 of the most suppressive of 84 soil samples assayed. Ultimately, six isolates were selected based on their efficacy in reducing pink rot in storage. Interestingly, the top six antagonist strains in reducing new pink rot infection were recovered from only three different soil extracts, all of which reduced zoospore production by at least 85% (Tables 1, 2). Individual antagonists would need to be evaluated for their ability to reduce zoospore production before a link between mechanisms of reducing zoospore production and reducing zoospore infection success could be postulated. Compared with the control tubers inoculated with *P. erythroseptica*, the six bacterial strains reduced disease by 26%-33% and all six antagonists were similarly effective in reducing pink rot as shown by similar $RPI_{Eff}$ values (Table 3). Efficacy of bacterial strains isolated in this study was better than that of biological control strain *Enterobacter cloacae* S11:T:07 (Schisler et al. 2009. ibid) when all strains were tested in the present study using fully grown culture broths that were diluted to the same extent. Though Schisler et al. (2009. ibid) investigated the effectiveness of S11:T:07 and nine other bacterial strains against pink rot (*P. erythroseptica*), this study is the first reported investigation designed to specifically isolate novel antagonists of pink rot.

Three of six strains effective in reducing the size of lesions incited by *P. erythroseptica* were identified as *Bacillus simplex* (Table 2). These strains significantly reduced pink rot severity when tested at concentrations one order of magnitude lower than found in full strength culture broths (Table 3). *Pantoea agglomerans* strain 10IL31 also reduced the size of pink rot lesions (Table 3). Strains 13IL01 and 10IL21 (*Pseudomonas lini* and *Pseudomonas koreensis* respectively) scored the lowest RPI values for efficacy though 13IL01 still significantly reduced pink rot disease (Table 3).

As a next step in selecting promising biological control candidates, we evaluated the growth characteristics, in liquid culture, of the six putative antagonists. Since a rapidly achieved high yield of biomass with cost effective production is critical for the commercial success of a biological control agent, our selection of isolates was based on evaluating the ability of a strain to rapidly produce cells after inoculation ($OD_8$), rapidly reach near maximum cell counts as demonstrated by cultures that quickly reached a stage of unbalanced growth with concomitant recover from oxygen depletion (DT), and produce high yields of biomass which was indicated by high CFU/ml ($CFU_{max}$) and biomass ($DW_{max}$) values in a representative liquid medium.

During the growth of bacterial strains in shake flasks, dissolved oxygen (DO) levels are less than maximal during periods of rapid cell growth and reach near maximal levels as one or more nutrients are depleted resulting in unbalanced growth, cell growth rates that are near zero, and the indication that the culture has reached near maximal cell numbers. Low DT values indicate that a strain rapidly reached unbalanced growth and therefore, near maximal cell counts. The depletion of nitrogen, carbon, or both in the medium would be one possible explanation for the end of rapid cell growth in culture and, concomitantly, recovery of dissolved oxygen levels from near zero to saturation as cell respiration rates slowed. Due to the accumulation of heat during bacterial growth in deep tank fermentors, considerable cooling and associated costs are required to maintain temperatures of 20-30° C. in an industrial bioreactor. Therefore, developing strains that rapidly produce high quantities of biomass should reduce utility expenses, one of the highest operating costs associated with utilizing commercial bioreactors.

When grown in the selected liquid medium, *B. simplex* strains 03WN13, 03WN23 and 03WN25 as well as *Pseudomonas lini* 13IL01 achieved the highest biomass value ($DW_{max}$) of the six candidates yet strain 03WN23 produced the lowest colony forming units ($CFU_{max}$) (Table 5). On the other hand, *P. koreensis* 10IL21 exhibited the highest $CFU_{max}$ but the lowest DWmax and the longest time before dissolved oxygen recovery (DT). Hence this strain, which also ranked as the least efficacious against *P. erythroseptica* (Table 3), scored the lowest overall $RPI_{Eff, Kin}$. All of the *B. simplex* strains (03WN13, 03WN23, and 03WN25) and *Pantoea agglomerans* 10IL31 ranked as the top four strains for $RPI_{DT}$ and $RPI_{OD8}$ (Table 5). Interestingly, *B. simplex* strain 03WN23 ranked last in $CFU_{max}$ despite ranking second in $DW_{max}$, perhaps due to the tendency of the strain to form long chains of cells that would score as a single colony forming unit in plate counts. Oxidative stress may also limit colony formation of still viable cells of *B. simplex* (Gomaa and Azab. 2007. Role of calcium carbonate in protecting the colony forming ability of *Bacillus simplex* TWW-04 exposed to oxidative stress. Adv. Biolog. Res. 1:49-55). *B. simplex* strain 03WN13 and *P. agglomerans* strain 0IL31 ranked first and second of the six antagonists studied in overall $RPI_{Eff, Kin}$ respectively, showing the consistency between ranking of $RPI_{Eff}$ and $RPI_{Kin}$ (Table 5). Variability in growth kinetics for the strains of *Bacillus* tested in this study had a large impact on the RPI values obtained for the various kinetic RPI's and contributed to the overall kinetic RPI values not being separable statistically. In similar ranking studies using exclusively Gram negative bacteria, kinetic performance was more consistent between the kinetic parameters measured and, as a result, overall kinetic performance means frequently differed significantly (Slininger et al. 1994. ibid).

Despite a lack of statistical separation of the overall $RPI_{Eff, Kin}$ values determined for the six novel biological control strains identified in the current study, the ranks of strains obtained by the RPI procedure are useful as a logically sound method for considering which strains to concentrate commercial development efforts on and, as a method for addressing which strain is the next best candidate to consider. If in the course of pre-commercial product development an altered medium is preferred for strain production or the conditions under which strain are to be used changes considerably, then it should be understood that the commercial ranking obtained for the putative antagonists in this study is subject to recalculation to meet the specific need of the producer of the product. The commercial ranking procedure employed in this study does not consider the possibility that a prospective producer or user would prefer a dried biological control product. Drying economics, the comparative survival rate of dried isolates and the disease suppressiveness of dried cells would all have a profound impact on the ranking of these strains but could also be incorporated into a RPI-based ranking procedure. Additionally, different kinetic parameters than those used here could be taken into account as alternative approaches for the economic analysis of the production process. Giving additional weight to those kinetic parameters considered most critical to a specific commercial fermentor when calculating and ranking isolate RPIs could also enhance the utility of the final rankings determined. Evaluation of software such as SuperPro Designer (Itelligen, Inc., Scotch Plains, N.Y.), which enables users to model and predict the costs of industrial production processes, could be useful for estimating the importance of the effect of differing kinetic values on the rankings of the development potential of biocontrol agents and associated industrial process costs.

An important but overlooked step regarding designing protocols for discovering biocontrol agents is to insure that selected strains amenable to liquid culture production and efficacious when produced in this manner. Antagonists of pink rot in the current study were isolated from biologically-based, suppressive soil extracts and then subjected to this two dimensional method of ranking biocontrol agent potential. The top strains identified warrant further investigation of their ability to control pink rot of potato using increased dosages in a small-pilot storage trial where conditions closely emulate those under which the strains would have to perform in field use. Tests integrating the use of these strains and active fungicides are also needed and may allow a reduction in the amount of fungicide needed to suppress pink rot (Al-Mughrabi et al. 2007. ibid; and Miller et al. 2006. ibid).

TABLE 1

Activity of 13 soil extracts in reducing pink rot disease development, zoospore production by *P. erythroseptica*, or both.

| Treatment | Reduction of disease severity[a] (%) | Reduction of zoospore production (%) |
|---|---|---|
| 1199-WI | NE[b] | 93 |
| 1261-WI | NE[b] | 86 |
| 1198-WI | NE[b] | 86 |
| 1248-WI | 6 | 14 |
| 1197-WI | 21 | 43 |
| Unit 169-WG | 18 | 29 |
| Pivot 3-WG | 26 | 76 |
| 2nd Pivot-WG | NE[b] | 76 |
| 96-1-WG | NE[b] | 88 |
| S Garden 2-IL | NE[b] | 88 |
| Duval 4-IL | 20 | 39 |
| Basil-IL | NE[b] | 24 |
| S Garden 1-IL | NE[b] | 90 |
| Control | 0 | 0 |

[a]Disease assays were conducted on tubers of cultivar Russet Norkotah.
[b]Treatment was not effective in reducing disease severity under assay conditions.

TABLE 2

Identification of bacterial strains that reduce pink rot disease in Russet Burbank tubers

| Strain | NRRL accession number[a] | Identification | Soil extract of strain origin |
|---|---|---|---|
| 03WN13 | B-59398 | *Bacillus simplex* | 1198-WI |
| 03WN23 | B-59399 | *Bacillus simplex* | 1198-WI |
| 03WN25 | B-59400 | *Bacillus simplex* | 1198-WI |
| 10IL21 | B-59401 | *Pseudomonas koreensis* | S Garden 2-IL |
| 10IL31 | B-59402 | *Pantoea agglomerans* | S Garden 2-IL |
| 13IL01 | B-59404 | *Pseudomonas lini* | S Garden 1-IL |

[a]ARS Culture Collection (NRRl), National Center for Agricultural Utilization Research, Peoria, IL, U.S.A.

TABLE 3

Comparison of relative performance indices for efficacy ($RPI_{Eff}$) and their rank for six bacterial antagonists assayed against *Phytophthora erythroseptica* on cultivar Russet Burbank.

| Strain | Diseased tissue (mm)[a] | Efficacy $RPI^{(rank)b}$ |
|---|---|---|
| 03WN13 | 40.9* | 51.0$^{(3)}$ A |
| 03WN23 | 42.8* | 49.1$^{(4)}$ A |
| 03WN25 | 39.4* | 52.1$^{(1)}$ A |
| 10IL21 | 44.5 | 47.9$^{(6)}$ A |
| 10IL31 | 39.0* | 51.4$^{(2)}$ A |
| 13IL01 | 43.4* | 48.4$^{(5)}$ A |
| Control | 58.4 | NA[c] |

[a]Values followed by an asterisk (*) are significantly different from the control (P ≤ 0.05, FPLSD)
[b]RPI = Relative performance index. The rank of each RPI value mean is presented parenthetically. Within the column, values followed by unlike letters are significantly different (P ≤ 0.05, FPLSD).
[c]NA = Not applicable

TABLE 4

Performance of six antagonists of pink rot for each of the four kinetic parameters evaluated.

| Strain | $CFU_{max}$[a] (log10) | $DW_{max}$[b] (g) | $DT$[c] (min) | $OD_8$[d] (620 nm) |
|---|---|---|---|---|
| 03WN13 | 8.2 | 8.9E−03 | 644 | 6.7 |
| 03WN23 | 6.5 | 8.5E−03 | 681 | 4.5 |
| 03WN25 | 8.6 | 7.3E−03 | 695 | 1.4 |
| 10IL21 | 10.4 | 4.8E−03 | 1364 | 2.6 |
| 10IL31 | 9.7 | 5.3E−03 | 562 | 5.6 |
| 13IL01 | 10 | 7.3E−03 | 940 | 2.6 |

[a]$CFUmax$ (log 10) = Log base 10 of the colony forming units of the isolate obtained per ml of a 48 h liquid culture.
[b]$DW_{max}$(g) = Total biomass production values of the isolate obtained per ml of 48 h liquid culture.
[c]$DT$ (min) = Time of the initiation of the recovery of dissolved oxygen values from near zero during the liquid culture production of the antagonist isolates. Recovery of oxygen values from near zero are indicative of near depletion of one or more nutrients in culture broths and associated marked reductions in cell growth rates.
[d]$OD8$ (620 nm) = Optical density of 8 h test cultures of each antagonist isolate.

TABLE 5

Comparison of the relative performance indices (RPI) for several different growth kineticparameters determined for each of six bacterial antagonists and the overall RPI kinetics value.

| Strain | RPI parameter | | | | Overall |
| | $CFU_{max}$ | $DW_{max}$ | $DT$ | $OD_8$ | $RPI_{Kin}$ |
|---|---|---|---|---|---|
| 03WM13 | 33.9$^{(5)}$ E | 76.9$^{(1)}$ A | 63.8$^{(2)}$ AB | 82.1$^{(1)}$ A | 64.1$^{(1)}$ A |
| 03WN23 | 6.7$^{(6)}$ F | 72.6$^{(2)}$ A | 60.2$^{(4)}$ B | 71.7$^{(2)}$ A | 52.8$^{(3)}$ A |
| 03WN25 | 41.8$^{(4)}$ D | 54.5$^{(3)}$ B | 60.4$^{(3)}$ B | 39.9$^{(4)}$ B | 49.1$^{(5)}$ A |
| 10IL21 | 77.5$^{(1)}$ A | 22.3$^{(6)}$ C | 4.4$^{(6)}$ D | 39.5$^{(5)}$ B | 35.9$^{(6)}$ A |
| 10IL31 | 64.4$^{(3)}$ C | 23.7$^{(5)}$ C | 71.4$^{(1)}$ A | 54.4$^{(3)}$ AB | 53.5$^{(2)}$ A |
| 13IL01 | 69.9$^{(2)}$ B | 51.3$^{(4)}$ B | 39.7$^{(5)}$ C | 35.9$^{(6)}$ B | 49.2$^{(4)}$ A |

[a]RPI = Mean relative performance index values are presented. The rank of each RPI value is presented parenthetically. Within a column, values followed by unlike letters are significantly different (P ≤ 0.05, FPLSD).

TABLE 6

The use of relative performance indices (RPI) to accomplish a two-dimensional assessment of isolate commercial potential based on the efficacy and growth kinetics of cells produced in liquid culture.

| Strain | $RPI_{Eff}$ | Overall $RPI_{Kin}$ | Overall $RPI_{Eff, Kin}$ | Commercial Potential Group[a] |
|---|---|---|---|---|
| 03WM13 | 51.0$^{(3)}$ A | 64.1$^{(1)}$ A | 57.6$^{(1)}$ | A |
| 03WN23 | 49.1$^{(4)}$ A | 52.8$^{(3)}$ A | 50.9$^{(3)}$ | A |
| 03WN25 | 52.1$^{(1)}$ A | 49.1$^{(5)}$ A | 50.6$^{(4)}$ | A |
| 10IL21 | 47.9$^{(6)}$ A | 35.9$^{(6)}$ A | 41.9$^{(6)}$ | A |
| 10IL31 | 51.4$^{(2)}$ A | 53.5$^{(2)}$ A | 52.4$^{(2)}$ | A |
| 13IL01 | 48.4$^{(5)}$ A | 49.2$^{(4)}$ A | 48.8$^{(5)}$ | A |

[a]Commercial potential groupings were determined by forming a dataset composed of $RPI_{Eff}$ and $RPI_{Kin}$ data for each strain and subjecting the data to ANOVA and mean separation using Fisher's Protected LSD (P ≤ 0.05, FPLSD). Means not sharing a common letter belong to different commercial potential groups.

It is understood that the foregoing detailed description is given merely by way of illustration and that modifications and variations may be made therein without departing from the spirit and scope of the invention.

We claim:

1. A biologically pure culture of a bacterium effective for control of pink rot on potato tubers, said bacterium selected from the group consisting of *Bacillus simplex* strain 03WN13 deposited at the Agricultural Research Service Culture Collection under deposit accession number NRRL B-50565, *Bacillus simplex* strain 03WN23 deposited at the Agricultural Research Service Culture Collection under deposit accession number NRRL B-50566, *Bacillus simplex* strain 03WN25 deposited at the Agricultural Research Service Culture Collection (NRRL) under deposit accession number NRRL B-50567, *Pseudomonas koreensis* strain 101L21 deposited at the Agricultural Research Service Culture Collection under deposit accession number NRRL B-50568, *Pantoea agglomerans* strain 101L31 deposited at the Agricultural Research Service Culture Collection under deposit accession number NRRL B-50569, and *Pseudomonas lini* strain 131L01 deposited at the Agricultural Research Service Culture Collection under deposit accession number NRRL B-50570.

2. A biologically pure culture of claim 1 wherein said bacterium is said *Bacillus simplex* strain 03WN13.

3. A biologically pure culture of claim 1 wherein said bacterium is said *Bacillus simplex* strain 03WN23.

4. A biologically pure culture of claim 1 wherein said bacterium is said *Bacillus simplex* strain 03WN25.

5. A biologically pure culture of claim 1 wherein said bacterium is said *Pseudomonas koreensis* strain 101L21.

6. A biologically pure culture of claim 1 wherein said bacterium is said *Pantoea agglomerans* strain 101L31.

7. A biologically pure culture of claim 1 wherein said bacterium is said *Pseudomonas lini* strain 131L01.

8. A method for suppressing pink rot infections on potatoes comprising applying to potato tubers, potato tuber parts or seed tubers, a biologically pure culture of at least one bacterial antagonist selected from the group consisting of *Bacillus simplex* strain 03WN13 deposited at the Agricultural Research Service Culture Collection under deposit accession number NRRL B-50565, *Bacillus simplex* strain 03WN23 deposited at the Agricultural Research Service Culture Collection under deposit accession number NRRL B-50566, *Bacillus simplex* strain 03WN25 deposited at the Agricultural Research Service Culture Collection (NRRL) under deposit accession number NRRL B-50567, *Pseudomonas koreensis* strain 101L21 deposited at the Agricultural Research Service Culture Collection (NRRL) under deposit accession number NRRL B-50568, *Pantoea agglomerans* strain 101L31 deposited at the Agricultural Research Service Culture Collection (NRRL) under deposit accession number NRRL B-50569, and *Pseudomonas lini* strain 131L01 deposited at the Agricultural Research Service Culture Collection (NRRL) under deposit accession number NRRL B-50570, in an amount effective to reduce the level of pink rot disease caused by *Phytophthora erythroseptica* on the potato relative to an untreated control.

9. The method of claim 8 wherein said bacterial antagonist is applied to potato tubers during storage.

10. The method of claim 8 wherein said bacterial antagonist is applied to the locus of potato tubers in the field.

11. The method of claim 8 wherein said bacterial antagonist is said *Bacillus simplex* strain 03WN13.

12. The method of claim 8 wherein said bacterial antagonist is said *Bacillus simplex* strain 03WN23.

13. The method of claim 8 wherein said bacterial antagonist is said *Bacillus simplex* strain 03WN25.

14. The method of claim 8 wherein said bacterial antagonist is said *Pseudomonas koreensis* strain 101L21.

15. The method of claim 8 wherein said bacterial antagonist is said *Pantoea agglomerans* strain 101L31.

16. The method of claim 8 wherein said bacterial antagonist is said *Pseudomonas lini* strain 131L01.

* * * * *